(12) United States Patent
Sadilek et al.

(10) Patent No.: US 12,154,692 B2
(45) Date of Patent: Nov. 26, 2024

(54) PRIVACY-FIRST ON-DEVICE FEDERATED HEALTH MODELING AND INTERVENTION

(71) Applicant: Google LLC, Mountain View, CA (US)

(72) Inventors: Adam Sadilek, San Jose, CA (US); Blaise Aguera-Arcas, Seattle, WA (US); Keith Allen Bonawitz, Watchung, NJ (US)

(73) Assignee: GOOGLE LLC, Mountain View, CA (US)

(*) Notice: Subject to any disclaimer, the term of this patent is extended or adjusted under 35 U.S.C. 154(b) by 772 days.

(21) Appl. No.: 17/051,188

(22) PCT Filed: Sep. 27, 2018

(86) PCT No.: PCT/US2018/053034
§ 371 (c)(1),
(2) Date: Oct. 28, 2020

(87) PCT Pub. No.: WO2020/046398
PCT Pub. Date: Mar. 5, 2020

(65) Prior Publication Data
US 2021/0090750 A1   Mar. 25, 2021

Related U.S. Application Data

(60) Provisional application No. 62/725,760, filed on Aug. 31, 2018.

(51) Int. Cl.
*G16H 50/80* (2018.01)
*G06F 21/62* (2013.01)
(Continued)

(52) U.S. Cl.
CPC ........ *G16H 50/80* (2018.01); *G06F 21/6245* (2013.01); *G06N 20/00* (2019.01);
(Continued)

(58) Field of Classification Search
CPC ........ G16H 50/80; G16H 10/60; G16H 50/20; G16H 50/30
See application file for complete search history.

(56) References Cited

U.S. PATENT DOCUMENTS

| | | | |
|---|---|---|---|
| 10,848,466 B2 | 11/2020 | Wang et al. | |
| 2006/0161527 A1* | 7/2006 | Dwork | G06F 21/6245 |

(Continued)

FOREIGN PATENT DOCUMENTS

| | | |
|---|---|---|
| CN | 107180152 | 9/2017 |
| CN | 107368752 | 11/2017 |

(Continued)

OTHER PUBLICATIONS

Ekkarat Boonchient, Ph.D., et al.; Digital Disease Detection: Application of Machine Learning in Community Health Informatics; 2016, 13th International Joint Conference on Computer Science and Software Engineering (Year: 2016).*

(Continued)

*Primary Examiner* — Evangeline Barr
(74) *Attorney, Agent, or Firm* — DORITY & MANNING P.A.

(57) ABSTRACT

The present disclosure provides systems and methods that leverage machine-learned models in conjunction with user-associated data and disease prevalence mapping to predict disease infections with improved user privacy. In one example, a computer-implemented method can include obtaining, by a user computing device associated with a user, a machine-learned prediction model configured to predict a probability that the user may be infected with a disease based at least in part on user-associated data associated with the user. The method can further include receiving, by the user computing device, the user-associated data associated with the user. The method can further include providing, by the user computing device, the user-associated (Continued)

data as input to the machine-learned prediction model, the machine-learned prediction model being implemented on the user computing device. The method can further include receiving, by the user computing device, a current disease prediction for the user as an output of the machine-learned prediction model. The method can further include providing, by the user computing device, data indicative of the current disease prediction for the user to a central computing system for use in updating a prevalence map that models prevalence of the disease over a plurality of geographic locations.

24 Claims, 9 Drawing Sheets

(51) Int. Cl.
    *G06N 20/00* (2019.01)
    *G16H 10/60* (2018.01)
    *G16H 40/67* (2018.01)
    *G16H 50/20* (2018.01)
    *G16H 50/30* (2018.01)

(52) U.S. Cl.
    CPC ............ *G16H 10/60* (2018.01); *G16H 40/67* (2018.01); *G16H 50/20* (2018.01); *G16H 50/30* (2018.01)

(56) References Cited

U.S. PATENT DOCUMENTS

| | | | | |
|---|---|---|---|---|
| 2013/0318027 | A1* | 11/2013 | Almogy | G16H 50/20 706/52 |
| 2015/0100330 | A1* | 4/2015 | Shpits | G16H 50/80 705/2 |
| 2015/0106020 | A1* | 4/2015 | Chung | G16H 40/67 702/19 |
| 2017/0204531 | A1 | 7/2017 | Suzuki | |
| 2017/0351833 | A1* | 12/2017 | Cahan | G06Q 50/14 |
| 2018/0075368 | A1* | 3/2018 | Brennan | G06N 5/022 |
| 2018/0181714 | A1* | 6/2018 | Pillarisetty | G16H 40/67 |
| 2018/0247194 | A1* | 8/2018 | Plebani | G06N 3/08 |

FOREIGN PATENT DOCUMENTS

| | | |
|---|---|---|
| CN | 108363928 | 8/2018 |
| KR | 2018/0058466 | 6/2018 |
| WO | WO 2018/093462 | 5/2018 |

OTHER PUBLICATIONS

Vinu Sundararaj, An Efficient Threshold Prediction Scheme for Wavelet Based ECG Signal Noise Reduction Using Variable Step Size Firefly Algorithm, 2016, International Journal of Intelligent Engineering and Systems, vol. 9, No. 3, pp. 117-126 (Year: 2016).*
International Search Report for PCT/US2018/053034, mailed on May 7, 2019, 2 pages.
International Preliminary Report on Patentability for PCT/US2018/053034, mailed on Mar. 2, 2021, 10 pages.
Machine Translated Chinese Search Report Corresponding to Application No. 2018800405748 on Mar. 21, 2023.
Chinese Search Report Corresponding to Application No. 2018800405748 on Dec. 19, 2023.

* cited by examiner

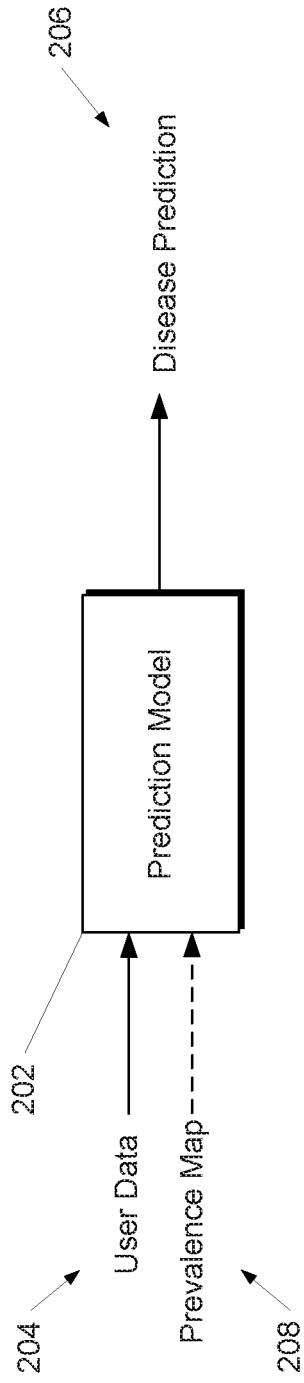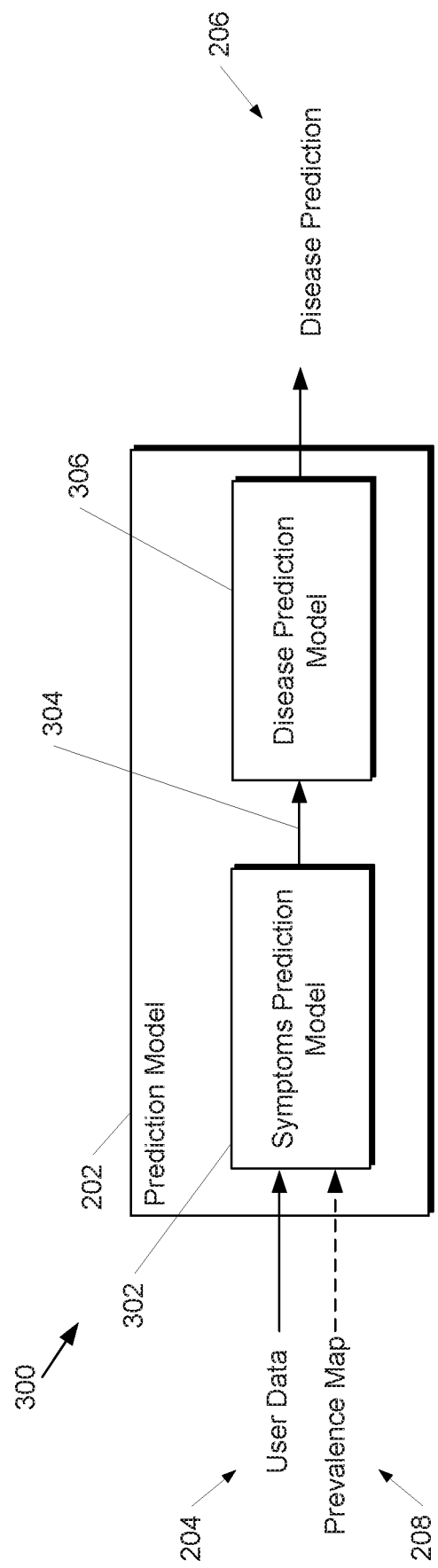

PRIVACY-FIRST ON-DEVICE FEDERATED HEALTH MODELING AND INTERVENTION

PRIORITY CLAIM

The present application is a national stage filing under 35 U.S.C. § 371 of Patent Cooperation Treaty Application Serial No. PCT/US2018/053034, filed on Sep. 27, 2018, which claims the benefit of U.S. Provisional Application No. 62/725,760 having a filing date of Aug. 31, 2018. Applicant claims priority to and the benefit of each of such applications and incorporate all such applications herein by reference in their entirety.

FIELD

The present disclosure relates generally to machine learning. More particularly, the present disclosure relates to the use of machine-learned models to enable personalized health modeling and exposure prediction with improved user privacy.

BACKGROUND

Use of a client-server model for localized epidemiological tracking, modeling, and outbreak identification can have multiple disadvantages, such as, for example, requiring a robust and regular data connection between a device and a server; the need to track location history and/or other log data of specific users and associate that history and data with certain measured physiological conditions and/or symptoms; the aggregation of that data at a third party service with possible identity and privacy concerns; and/or the like. Furthermore, it may not feasible to upload some types of data, for example continuous audio or video, from a device to a server on an ongoing basis.

Thus, improved systems for on-device data collection, learning, analysis, and reporting of symptoms can provide both significant improvements in public health while also reducing the financial cost associated with treating or otherwise responding to the diseases.

SUMMARY

Aspects and advantages of embodiments of the present disclosure will be set forth in part in the following description, or can be learned from the description, or can be learned through practice of the embodiments.

One example aspect of the present disclosure is directed to a computer-implemented method to generate disease prediction. The method includes obtaining, by a user computing device associated with a user, a machine-learned prediction model configured to predict a probability that the user exhibits a risk of disease infection based at least in part on user-associated data associated with the user. The method includes obtaining, by the user computing device, the user-associated data associated with the user. The method includes providing, by the user computing device, the user-associated data as input to the machine-learned prediction model, the machine-learned prediction model being implemented on the user computing device. The method includes receiving, by the user computing device, a current disease prediction for the user as an output of the machine-learned prediction model. The method includes providing, by the user computing device, data indicative of the current disease prediction for the user to a central computing system for use in updating a prevalence map that models prevalence of the disease over a plurality of geographic locations.

The method may further comprise, prior to providing the data indicative of the current disease prediction for the user to the central computing system for use in updating the prevalence map: obtaining, by the user computing device, the prevalence map from the central computing system; obtaining, by the user computing device, a location history associated with the user; and providing, by the user computing device, the prevalence map and the location history as input to the machine-learned prediction model alongside the user-associated data, the current disease prediction output by the machine-learned prediction model being based at least in part on each of the user-associated data, the location history associated with the user, and the prevalence map. The method may further comprise: obtaining, by the user computing device, the prevalence map from the central computing system, wherein the prevalence map models prevalence of the disease over the plurality of geographic locations and also over time; and generating, by the user computing device, for each of a plurality of combinations of time and geographic location, a respective probability of the user having contracted the disease at such combination of time and geographic location based at least in part on the prevalence map.

Providing, by the user computing device, the data indicative of the current disease prediction for the user to the central computing system for use in updating the prevalence map may comprise performing, by the user computing device, a secure aggregation technique or a differential privacy technique to provide the data indicative of the current disease prediction for the user to the central computing system. Performing, by the user computing device, the secure aggregation technique or the differential privacy technique to provide the data indicative of the current disease prediction for the user to the central computing system may comprise: providing, by the user computing device with a first probability, the data indicative of the current disease prediction for the user to the central computing system; and providing, by the user computing device with a second probability, a falsified disease prediction for the user to the central computing system.

The user-associated data may comprise one or more of: a device location of the user computing device; a search engine query history associated with the user; sensor data that is descriptive of a physical attribute of the user; environmental conditions associated with a current location of the user; and a time of day. The sensor data may comprise one or more of: audio data descriptive of a vocalization of the user; image data that depicts the user; accelerometer data descriptive of motion of the user; heart rate data; blood pressure data; and electrocardiogram data. The machine-learned prediction model may comprise one or both of: a symptoms prediction model that predicts symptoms based on user-associated data; and a disease prediction model that predicts one or more diseases based on symptoms. The machine-learned prediction model may have been trained using ground truth public health data.

The method may further comprise: re-training, by the user computing device, the machine-learned prediction model based at least in part on a loss function that evaluates a difference between the current disease prediction for the user and a label; transmitting, by the user computing device, a model update descriptive of one or more changes to the machine-learned prediction model made during the re-training to the central computing system for use in determining an aggregate update to the machine-learned prediction model; and receiving, by the user computing device, an updated version of the machine-learned prediction model from the central computing system, the updated version of the machine-learned prediction model based at least in part on the aggregate update.

The method may further comprise: providing, by the user computing device, one or more notifications to the user based at least in part on the current disease prediction. The method may further comprise: maintaining, by the central computing system, a record of changes to the prevalence map over time; and training, by the central computing system, an additional machine-learned model based on the record of changes to the prevalence map to configure the additional machine-learned model to predict one or more future changes to one or more future prevalence maps.

Another example aspect of the present disclosure is directed to a computing device. The computing device includes one or more processors. The computing device includes one or more non-transitory computer-readable media that collectively store instructions that, when executed by the one or more processors, cause the computing device to perform operations. The operations include obtaining a machine-learned prediction model. The operations include obtaining a prevalence map. The operations include obtaining one or more types of user-associated data. The operations providing the one or more types of user-associated data and the prevalence map as input to the machine-learned prediction model. The operations include determining a current disease prediction as output of the machine-learned prediction model. The operations include providing one or more indications to a user based the current disease prediction.

The current disease prediction provided as output of the machine-learned prediction model may include a probability of being infected; and a probability of having contracted an infection for each of one or more time and geographic buckets considered by the machine-learned prediction model. The operations may further include: providing data indicative of the probability of having contracted an infection for each of one or more time and geographic buckets considered by the machine-learned prediction model for use in updating the prevalence map. A central computing system may aggregate the data indicative of the probability of having contracted the infection for each of one or more time and geographic buckets in a secure manner to update the prevalence map. Providing data indicative of the probability of having contracted an infection for each of one or more time and geographic buckets considered by the machine-learned prediction model for use in updating the prevalence map may include providing randomized probabilities for one or more of the time and geographic buckets.

Another example aspect of the present disclosure is directed to a computing system that includes a central computing system configured to transmit a machine-learned prediction model and a prevalence map to each of a plurality of user computing devices respectively associated with a plurality of users, wherein each machine-learned prediction model is configured to predict a probability that the respective user may be infected with a disease based at least in part on respective user-associated data associated with the respective user, and wherein each prevalence map models prevalence of the disease over a plurality of geographic locations. The central computing system is further configured to receive a plurality of current health predictions from the plurality of user computing devices, the current health prediction received from each user computing device generated by the machine-learned prediction model transmitted to such user computing device based at least in part on the prevalence map transmitted to such user computing device. The central computing system is further configured to update the prevalence map based at least in part on the plurality of current health predictions to form an updated version of the prevalence map. The central computing system is further configured to transmit the updated version of the prevalence map to each of the plurality of user computing devices.

The central computing system may be configured to receive the plurality of current health predictions from the plurality of user computing devices via a secure aggregation or a differential privacy technique. The system may further include: the plurality of user computing devices, wherein each user computing device is configured to provide its respective current health prediction to the central computing system via a secure aggregation or a differential privacy technique.

Another example aspect of the present disclosure is directed to a computer-implemented method. The method includes obtaining, by a user computing device associated with a user, a machine-learned prediction model configured to predict a probability that the user may be infected with a disease based at least in part on user-associated data associated with the user. The method further includes receiving, by the user computing device, the user-associated data associated with the user. The method further includes providing, by the user computing device, the user-associated data as input to the machine-learned prediction model, the machine-learned prediction model being implemented on the user computing device. The method further includes receiving, by the user computing device, a current disease prediction for the user as an output of the machine-learned prediction model. The method further includes providing, by the user computing device, one or more notifications to the user based at least in part on the current disease prediction.

Another example aspect of the present disclosure is directed to a computer-implemented method. The method includes receiving, by one or more computing devices, user data. The method includes determining, by the one or more computing devices, correlations between the user data and one or both of disease or location. The method includes storing, by the one or more computing devices, the correlations. The method includes iteratively updating, by the one or more computing devices, the correlations upon receipt of new user data to form a disease prediction model and/or a prevalence map.

Other aspects of the present disclosure are directed to various systems, apparatuses, non-transitory computer-readable media, user interfaces, and electronic devices. It will be appreciated that aspects described above in the context of one form may be implemented in any other convenient form. Features described in the context of one aspect may be implemented in the context of another aspect.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which:

FIG. 2 depicts a block diagram of an example prediction model according to example embodiments of the present disclosure;

FIG. 3 depicts a block diagram of an example prediction model according to example embodiments of the present disclosure;

Figure 1A:
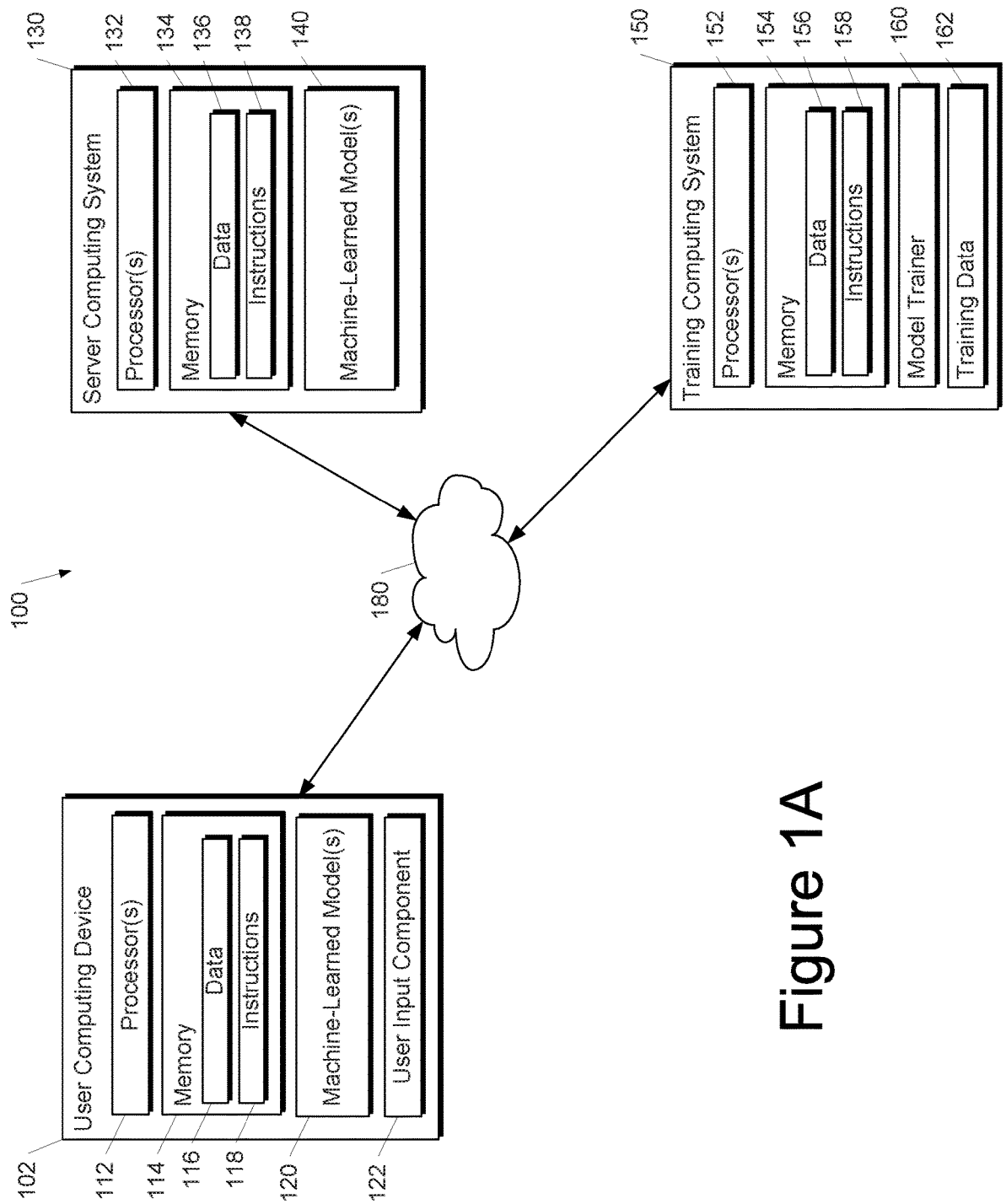
FIG. 1A depicts a block diagram of an example computing system according to example embodiments of the present disclosure.

Reference numerals that are repeated across plural figures are intended to identify the same features in various implementations.

DETAILED DESCRIPTION

Overview

Example aspects of the present disclosure are directed to systems and methods that include or otherwise leverage machine-learned models in conjunction with user-associated data and disease prevalence mapping to predict disease infections. In particular, the systems and methods of the present disclosure can facilitate on-device data collection, learning, analysis, and/or reporting of symptoms and alerts to possible exposure and/or contraction of a disease by a user, enabling personalized health monitoring without any personal data leaving the user device. For example, a user device can locally store and implement a machine-learned prediction model that can predict a probability that a user may have a disease (e.g., indicates a risk and/or likelihood of disease infection) based on locally stored user data, thereby preserving the privacy of such data. The prediction model may take as input a disease prevalence map alongside the user data. In addition, federated learning and/or privacy-preserving update techniques can be used to maintain and update the prediction model and/or prevalence map over time. For example, the respective outputs of prediction models across a large number of user devices can be securely aggregated and used to update the disease prevalence map (e.g., based on user consent, etc.). As another example, respective local updates to the machine-learned prediction model across the large number of user devices can be aggregated according to a federated learning scheme to improve the accuracy of the prediction model over time. The updated prediction models and/or prevalence maps can then be sent back to the user devices for more accurate on device disease prediction. Thus, improved user-specific prediction and population-level mapping can be achieved over time while preserving user privacy.

A disease can be a communicable disease or illness; an infectious disease; a transmissible disease; a disease caused by a pathogen such as bacterial pathogens, viral pathogens, fungi or protozoa pathogens; an allergic disease; and/or other forms of diseases. Example diseases include malaria, Ebola, cholera, influenza, Lyme disease, varicella, variola, dengue fever, foodborne illness, etc.

More particularly, according to one aspect of the present disclosure, if a user chooses to participate in the proposed system, a machine-learned prediction model can be implemented locally on a user computer device (e.g., smartphone, tablet, etc.) to predict a probability that the user currently may have a disease (e.g., indicates a risk and/or likelihood of disease infection) based on locally stored data that is associated with the user. As examples, this user data can include user Internet history (e.g., submitted queries or other search history), direct sensor data (e.g., microphone data, camera data (e.g., infrared, ultraviolet, and/or visible light video data), accelerometer data, RADAR data, etc.), dedicated sensor data (e.g., heart rate, blood pressure, electrocardiogram, thermal properties, etc.), a user location history, and/or other forms of user data. In some implementations, a user can be provided with the ability to maintain selected data locally (e.g., selected data specific to the user, selected data specific to one or more diseases, etc.) such that the selected data is not shared beyond the user's device. In some implementations, the user device may also provide as input to the machine-learned model or otherwise leverage background health information, such as prevalence maps, for use in predicting whether a user has contracted a disease.

In some implementations, a computing system can obtain search engine data and/or location data from or in the form of logs stored in one or more databases associated with a search engine service and/or location service. As examples, the search engine data can include data descriptive of search queries; scrolling actions; result selection actions; time spent on user-selected results; content of user-selected results; and/or other search engine information.

The search engine data or other user data does not need to be explicitly about or otherwise directly identify a particular disease. Instead, for example, the data can generally describe a number of related symptoms, indicators, or other signals or data points suggestive of a disease. When these related items are correlated in time and/or location they may suggest that one or more users are suffering from a disease which can cause the symptoms, indicators, or other signals described by the user data. For example, the search queries "sneezing" and "runny nose" do not explicitly identify the disease of "seasonal allergies." However, when combined with other contextual signals or indicators such as, for example, search data indicating that a user selected and read a search result about allergic reactions and/or transaction data indicating that the user purchased allergy medications online, these signals can collectively indicate that the user is suffering from seasonal allergies.

The machine-learned prediction model can be configured to predict a probability that the user may be infected with one or more diseases (e.g., exhibits a risk of disease infection) based at least in part on the user-associated data associated with the user and/or other input data. As one example, the disease prediction can provide a probability that the user is currently infected with a disease. In another example, the disease prediction can provide, for each of a plurality of combinations of time and geographic location, a respective probability of the user having contracted a disease at such combination of time and geographic location. In some implementations, this information (e.g., probability of contraction at each combination) can alternatively and/or additionally be generated based on the prevalence map. For example, user signals can represent noisy bounds on where and when the infection could have occurred and the global prevalence map can provide additional evidence which can be combined, for example, using a Bayesian model.

In some implementations, the on-device illness detection may allow for providing one or more indications to a user based on a prediction of contracting an illness. For example, the user device can inform the user of the likelihood of infection and suggest remedial actions, such as visiting medical professionals, reducing risk behaviors, and/or the like. Thus, the disease prediction can be used to provide notifications to the user (e.g., to notify the user to seek medical care or to provide information about treatment of the disease).

In some implementations, the machine-learned prediction model can include one or both of a symptoms prediction model that predicts symptoms based on the user-associated data and/or a disease prediction model that predicts a risk and/or probability of infection with one or more diseases based on symptoms. Thus, the model(s) might connect from user data to symptoms and/or from symptoms to illnesses. Thus, in some implementations, a user device may determine disease/illness symptoms based on the collected data and/or signals. For example, microphone data may be used in identifying a cough, slurring of speech, lethargy, and/or the like. Camera data may be used in identifying jaundice, swelling, marks, vision difficulty, and/or the like. Accelerometer data may be used in identifying stress, shivering, shaking, lethargy, and/or the like. Alternatively, the prediction model may be a single model configured to predict disease infection directly from the user data. In any of these configurations, end-to-end training can be used to train on training data that labels user data with disease information. In some implementations, the prediction model can be re-trained based on "ground-truth" labels which can come from several sources including, as examples, the user self-reporting, taking the predicted value as the actual value, and/or optimizing the health states of all individuals given the constraints given by the global prevalence model (e.g., including historical patterns and real-time signals).

In one example, the proposed system can include a number of different modules that can be loaded on a user device adaptively, and for example, governed by one or more user consent settings. The modules may each use different sensors and/or data, different machine-learned models, and/or different reporting, notification, and action paths. Furthermore, in some implementations, more than one module may run at a time on a user device. In some implementations, a core library or set of modules may be provided to enable health monitoring and detection, with additional modules being available based on user needs, user resources, user consent settings, and/or the like. For example, there may be modules to provide for data collection (e.g., for different data streams, such as audio, video, biometric sensors, and/or the like), modules specific to one or more types of illnesses/diseases, modules for types of data reporting, and/or the like.

Thus, capabilities can be provided on a user device to facilitate on-device data collection, learning, analysis, and reporting of symptoms and alerts to possible exposure/contraction of disease (such as viruses and other transmittable health risks). In some implementations, these on-device capabilities can provide various advantages, such as, increased privacy for users, improved detection without a need for a regular data connection (e.g., in areas lacking reliable data connectivity, etc.), an increased scope of coverage (both as to the number of individuals and geographic scope) for the identification of disease outbreaks, an increased and more nuanced suite of symptoms that can be monitored and conditions that can be identified locally, and/or support for new data collection modalities such as continuous monitoring, incidental monitoring (such as monitoring as part of user's otherwise traditional use of a cellular phone or similar device), triggered monitoring, and/or the like. As an example, new data collection modalities and analysis can include measuring body temperature while a user is otherwise using a device and/or keeping the device on his person, triggering analysis on the detection of the sound of a cough and using audio attributes of a cough as a signal, similarly using camera images for triggers and analysis, and/or the like.

According to another aspect, the user computing device can transmit the disease prediction to a central computing system in a privacy-preserving way (e.g., using secure aggregation and/or differential privacy techniques). The central computing system can use the received disease prediction and additional predictions received from a number of other user devices to update a prevalence map that models prevalence of the disease over a plurality of geographic locations. In such way, through the use of on-device inference (e.g., which does not require transmission of user data from the device) and through the use of privacy-preserving upload techniques, the proposed system can generate a prevalence map that provides up-to-date mapping of prevalence of a disease among a population and/or geographic area. This prevalence map can be used for any number of beneficial uses, including, for example, guiding large-scale disease treatment or mitigation efforts. In some implementations, a user can be provided with the ability to maintain selected data locally on the user computing device (e.g., selected data associated with the user, selected data specific to one or more diseases, etc.) such that the selected data is not shared beyond the user computing device.

Thus, the user device can provide the data indicative of the current disease prediction to a central computing system to be used in updating a global machine-learned model to infer disease state. For example, the global machine-learned model can be updated based on the probabilities received from user devices of having contracted an infection in each time frame and geographic area considered by the machine learned model. The machine-learned model for predicting a probability that a user is currently infected can be updated, for example, according to a federated learning scheme and using the probability of a user currently being infected obtained from a user device. As the global machine-learned model becomes more accurate, it becomes better able to impute where and/or when a user may have contracted the disease, as well as a probability that the user may be currently infected (for example, because the user has or has not been in a known-infectious place-time). Similarly, as the global model gets better at imputing whether the user may be currently infected, the model can improve in predicting infection given a user's query history.

According to an aspect of the present disclosure, federated learning can be applied with the machine-learned prediction models (e.g., that can infer disease state from input data) stored locally on user devices to provide for locally training the machine-learned models based on data that is associated with a user and that is obtained, collected, and/or stored on the local user device. The updates to the locally stored machine-learned model can then be provided to a central computer system and securely aggregated with model updates from other user devices to improve a global version of the machine-learned model. The systems and methods of the present disclosure can thus provide for using federated learning coupled with on-device inference, together with secure aggregation, to enable robust health modeling while maintaining user privacy.

Thus, in some implementations, a health modeling and intervention system can iterate progressively to refine privacy-preserving health maps (e.g. prevalence/risk maps, occupancy maps, mobility maps, etc.). A current version of a machine-learned model can be used to run inference over participating user devices and generate updates. These partial updates can be securely aggregated into a map (e.g., over geographical areas securely extracted and aggregated from device location sensors). The map can then be distributed back to the user devices to refine the machine-learned model. In some implementations, historical publicly available health data can be used in training and/or calibrating the global machine-learned model. For example, the global machine-learned models can be calibrated on ground truth from historical public health data to directly optimize incidence rate prediction without making inferences about individuals on a centralized computing system (e.g., without requiring a centralized database of inferences about individuals).

In an example, in some implementations, an iterative process can alternate between updating the local (user device) model and the global model. For example, federated learning can be used as an iterative optimization process where the most likely incidence rate of a variety of health conditions can be inferred, subject to noisy evidence securely aggregated over large numbers of devices. In particular, a user device can obtain a current version of a global machine-learned model used to infer disease state from a collection of data and signals. The user device can obtain (e.g., receive, collect, etc.) pertinent on-device user-associated data and signals (e.g., device location, user query history, sensor data descriptive of user physical attributes, environmental data, time of day, etc.). The user device can then generate prediction data with regard to the current disease infection state of the user (e.g., whether the user may be infected or not) based on inputting the obtained data and signals to the current local version of the machine-learned model on the user device. The user device can provide data indicative of a current disease prediction based on output from the local machine-learned model, including a probability of a user being currently infected. In some implementations, the machine-learned model output can include a probability of having contracted the infection in each time frame and geographic area considered by the machine learned model when generating the prediction data.

In some implementations, the systems and methods of the present disclosure can provide for assisting in the modeling of population level illness trends (e.g., epidemiology). For example, according to an aspect of the present disclosure, the systems and methods can provide for gathering geo-temporal statistics from on-device/user-local illness detection in a privacy preserving manner, such as through the use of secure aggregation and/or differential privacy techniques. Such geo-temporal statistics can be used in iteratively re-training the machine-learned models used in on-device illness detection. In some implementations, such geo-temporal statistics can be constrained to match existing prevalence maps. In some implementations, the systems and methods can allow for training machine-learned models to model the evolution of prevalence maps over time.

This structure leverages a mutually reinforcing cycle. As the global prevalence map gets more accurate, the prediction models are better able to impute where/when a user contracted the disease, as well as whether the user may be currently infected (because, e.g., the user has or has not been in a known-infectious place-time.) Similarly, as the prediction models more accurately impute a probability that the user is currently infected, the prevalence map can be improved based on the more accurate predictions.

In some implementations, based on the development of such population level illness trends, the systems and methods of the present disclosure can provide for generating user warnings about visiting locations with high levels of illness, for example, based on knowing a user's future travel plans. The systems and methods of the present disclosure can also provide scalability through local on-device illness detection to enable disease intervention in areas with reduced resources, for example, areas where it may not be feasible to do widespread epidemiological monitoring. Additionally, the systems and methods of the present disclosure can provide for improved illness detection in areas having poor data connectivity by providing for local on-device illness detection that does not require concurrent data connectivity.

In some implementations, the prediction model may learn to identify an infection earlier relative to the onset of that infection. For example, there may be a set of symptoms that are easy to identify as part of a disease, but which only show up late in the natural course of the infection of an individual. There may also be more subtle symptoms that show up earlier in the course of infection. The prediction model may learn to get better at having prediction(disease|symptoms[t=0 . . . T1])=prediction(disease|symptoms[t=0 . . . T2]) for time T2>T1. That is, the prediction model may learn to make the same predictions that it would be able to make at time T2, but with only the evidence available up through T1.

According to another aspect of the present disclosure, the systems and methods described herein can enable various applications based on on-device health modeling. For example, the systems and methods of the present disclosure can allow for machine learning of epidemiological models over data available locally on user devices, for example, leveraging text typed on the user devices and the GPS-like location history of the devices. The systems and methods of the present disclosure can provide assistance in producing privacy-preserving occupancy mobility maps, for example, aggregating statistics of how many devices moved from geographical area A to geographical area B over time interval T (e.g., important for disease modeling and infrastructure planning). In some implementations, the systems and methods of the present disclosure can allow for deploying securely aggregated risk maps for disease prevention (e.g., mosquito abatement campaigns, public education, flu shots and other vaccinations, mosquito netting distribution, adaptive medicine distribution, data-driven medicine distribution, etc.).

According to another aspect of the present disclosure, the systems and methods described herein can provide several mechanisms to protect user privacy. For example, all personal data can remain under the user's control and remain local to the user's device. Further, if the user so chooses, randomized responses can be provided from the user device to a central computing system (e.g., cloud server, etc.) and securely aggregated into population-level statistics (e.g., incidence rate, prevalence map, etc.). In some implementations, this can be achieved by the user device purposefully adding noise to the provided responses. For example, the user device can report a true location with probability p and report a false location (e.g., randomly generated location) with probability 1−p. Similarly, true health information can be reported with probability q and false health information reported with probability 1−q. In this fashion, each user response is too noisy to make meaningful inferences about individuals, but at a population level, the responses can be aggregated into actionable risk maps and other models. This randomized response protocol can be an important element that protects users' privacy because even if communication was intercepted and a response was read by an attacker, the attacker would at most learn a minimal amount of information about an individual (e.g., for any query about an individual user, the information gained would only improve the ability to answer the query accurately by no more than a very minimal amount).

Additionally, if the user so chooses, only heavily aggregated statistics (such as model training updates) may be provided to the central computing system. For example, noise drawn from a Laplacian distribution can be added to data to provide strong differential privacy guarantees by bounding the probability that the procedure would have produced a different output if the user's data had not been included. Furthermore, only patterns involving a sufficiently large number of individuals may be considered. As such, no individual user data may be inspected or modeled, only heavily aggregated statistics of large populations. Further, in some implementations, all communications may be encrypted.

The systems and methods of the present disclosure provide a number of technical effects and benefits. As one example, the systems described herein can work in real time to predict the probability that a user has contracted a disease. By working in real time on a local user device, the systems and methods of the present disclosure can lead to early identification and, therefore, early or preemptive abatement of diseases. Additionally, the systems and methods of the present disclosure can provide a technical benefit of improved illness detection in areas having poor data connectivity (e.g., lacking regular data connections, etc.) by providing for local on-device illness detection that does not require concurrent connectivity with a remote computing system.

As another technical effect and benefit, the systems and methods of the present disclosure provide a robust process which can allow for development of epidemiological models over data available locally on user devices without compromising user privacy. The systems and methods provide for increased scalability which can enable improved epidemiological monitoring and enable disease interventions even in low-resource areas.

With reference now to the Figures, example embodiments of the present disclosure will be discussed in further detail.

Example Devices and Systems

FIG. 1A depicts a block diagram of an example computing system 100 that can facilitate on-device data collection, learning, analysis, and/or reporting of symptoms and alerts to possible exposure and/or contraction of a disease by a user according to example embodiments of the present disclosure. The system 100 is provided as one example only. Other computing systems that include different components can be used in addition or alternatively to the system 100. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, a FPGA, a controller, a microcontroller, etc.) and can be one processor or a plurality of processors that are operatively connected. The memory 114 can include one or more non-transitory computer-readable storage mediums, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

In some implementations, the user computing device 102 can store or include one or more machine-learned models 120, such as a disease prediction machine-learned model as discussed herein. For example, the machine-learned models 120 can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks. Example machine-learned models 120 are discussed with reference to FIGS. 2 and 3.

In some implementations, the one or more machine-learned models 120 can be received from the server computing system 130 over network 180, stored in the user computing device memory 114, and then used or otherwise implemented by the one or more processors 112. In some implementations, the user computing device 102 can implement multiple parallel instances of a single machine-learned model 120.

More particularly, as described herein, a user computing device 102 can locally store and implement a machine-learned prediction model that can predict a probability that a user currently may have a disease based on locally stored data that is associated with the user. In some implementations, the user computing device 102 may also provide as input to the machine-learned model or otherwise leverage background health information, such as prevalence maps, for use in predicting whether a user has contracted a disease.

Additionally or alternatively, one or more machine-learned models 140 can be included in or otherwise stored and implemented by the server computing system 130 that communicates with the user computing device 102 according to a client-server relationship. For example, the machine-learned models 140 can be implemented by the server computing system 140 as a portion of a web service. Thus, one or more models 120 can be stored and implemented at the user computing device 102 and/or one or more models 140 can be stored and implemented at the server computing system 130.

The user computing device 102 can also include one or more user input component 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, a camera, or other means by which a user can provide user input.

The server computing system 130 includes one or more processors 132 and a memory 134. The one or more processors 132 can be any suitable processing device (e.g., a processor core, a microprocessor, an ASIC, a FPGA, a controller, a microcontroller, etc.) and can be one processor or a plurality of processors that are operatively connected. The memory 134 can include one or more non-transitory computer-readable storage mediums, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise include one or more machine-learned models 140. For example, the models 140 can be or can otherwise include various machine-learned models. Example machine-learned models include neural networks or other multi-layer non-linear models. Example neural networks include feed forward neural networks, deep neural networks, recurrent neural networks, and convolutional neural networks. Example models 140 are discussed with reference to FIGS. 2 through 5.

The user computing device 102 and/or the server computing system 130 can train the models 120 and/or 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, a FPGA, a controller, a microcontroller, etc.) and can be one processor or a plurality of processors that are operatively connected. The memory 154 can include one or more non-transitory computer-readable storage mediums, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 120 and/or 140 stored at the user computing device 102 and/or the server computing system 130 using various training or learning techniques, such as, for example, backwards propagation of errors. In some implementations, performing backwards propagation of errors can include performing truncated backpropagation through time. The model trainer 160 can perform a number of generalization techniques (e.g., weight decays, dropouts, etc.) to improve the generalization capability of the models being trained.

In particular, the model trainer 160 can train the machine-learned models 120 and/or 140 based on a set of training data 162. The training data 162 can include, for example, geo-temporal statistics (e.g., securely aggregated user disease prediction data, etc.), historical publicly available health data, prevalence maps, risk maps, and/or the like.

In some implementations, if the user has provided consent, the training examples can be provided by the user computing device 102. Thus, in such implementations, the model 120 provided to the user computing device 102 can be trained by the training computing system 150 on user-specific data received from the user computing device 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory, and executed by one or more processors. In other implementations, the model trainer 160 includes one or more sets of computer-executable instructions that are stored in a tangible computer-readable storage medium such as RAM hard disk or optical or magnetic media.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 1A illustrates one example computing system that can be used to implement the present disclosure. Other computing systems can be used as well. For example, in some implementations, the user computing device 102 can include the model trainer 160 and the training dataset 162. In such implementations, the models 120 can be both trained and used locally at the user computing device 102. In some of such implementations, the user computing device 102 can implement the model trainer 160 to personalize the models 120 based on user-specific data. Any components illustrated as being included in one of device 102, system 130, and/or system 150 can instead be included at one or both of the others of device 102, system 130, and/or system 150.

Figure 1B:
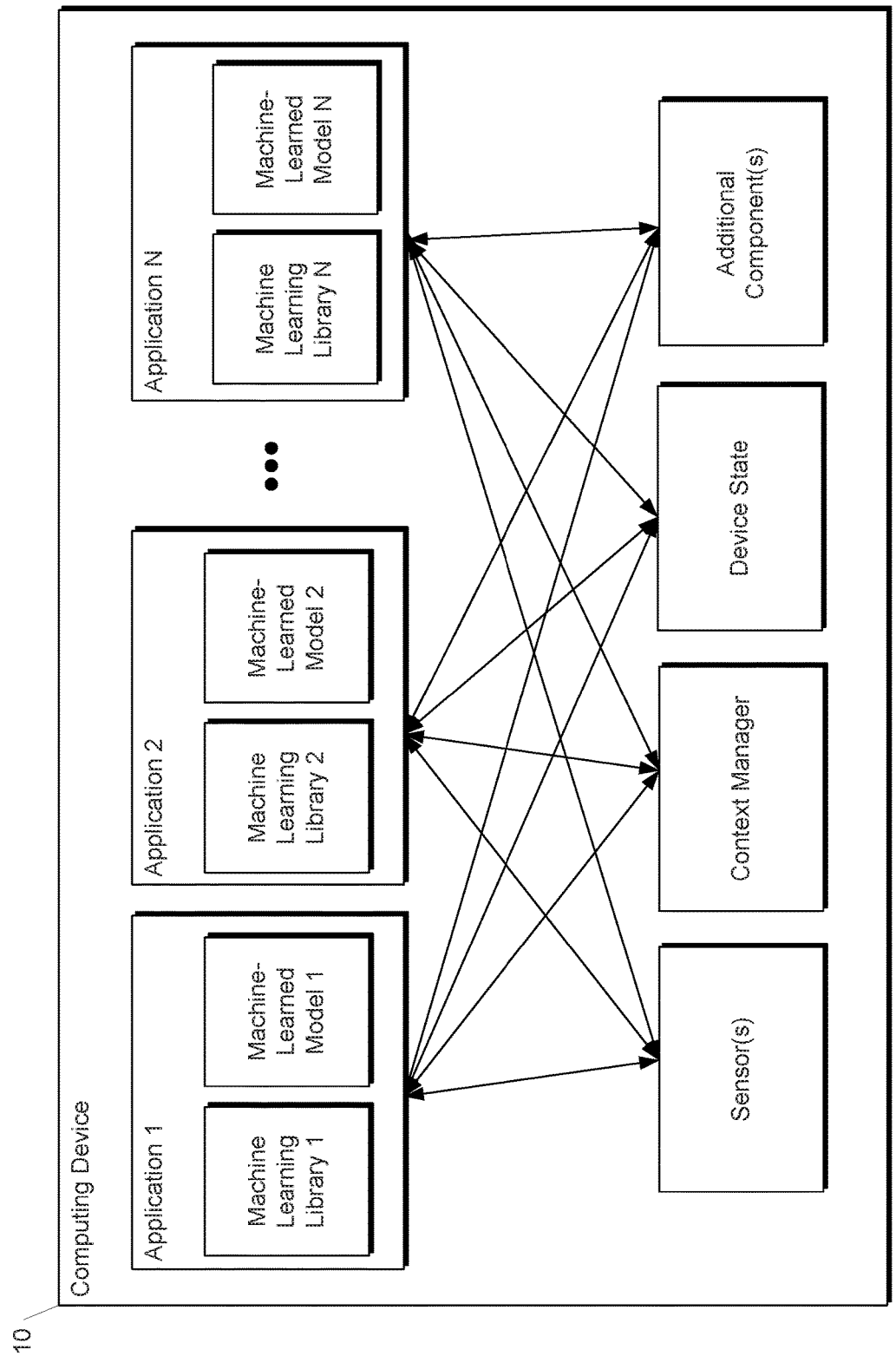
FIG. 1B depicts a block diagram of an example computing device according to example embodiments of the present disclosure.

FIG. 1B depicts a block diagram of an example computing device 10 according to example embodiments of the present disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 1B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 1C:
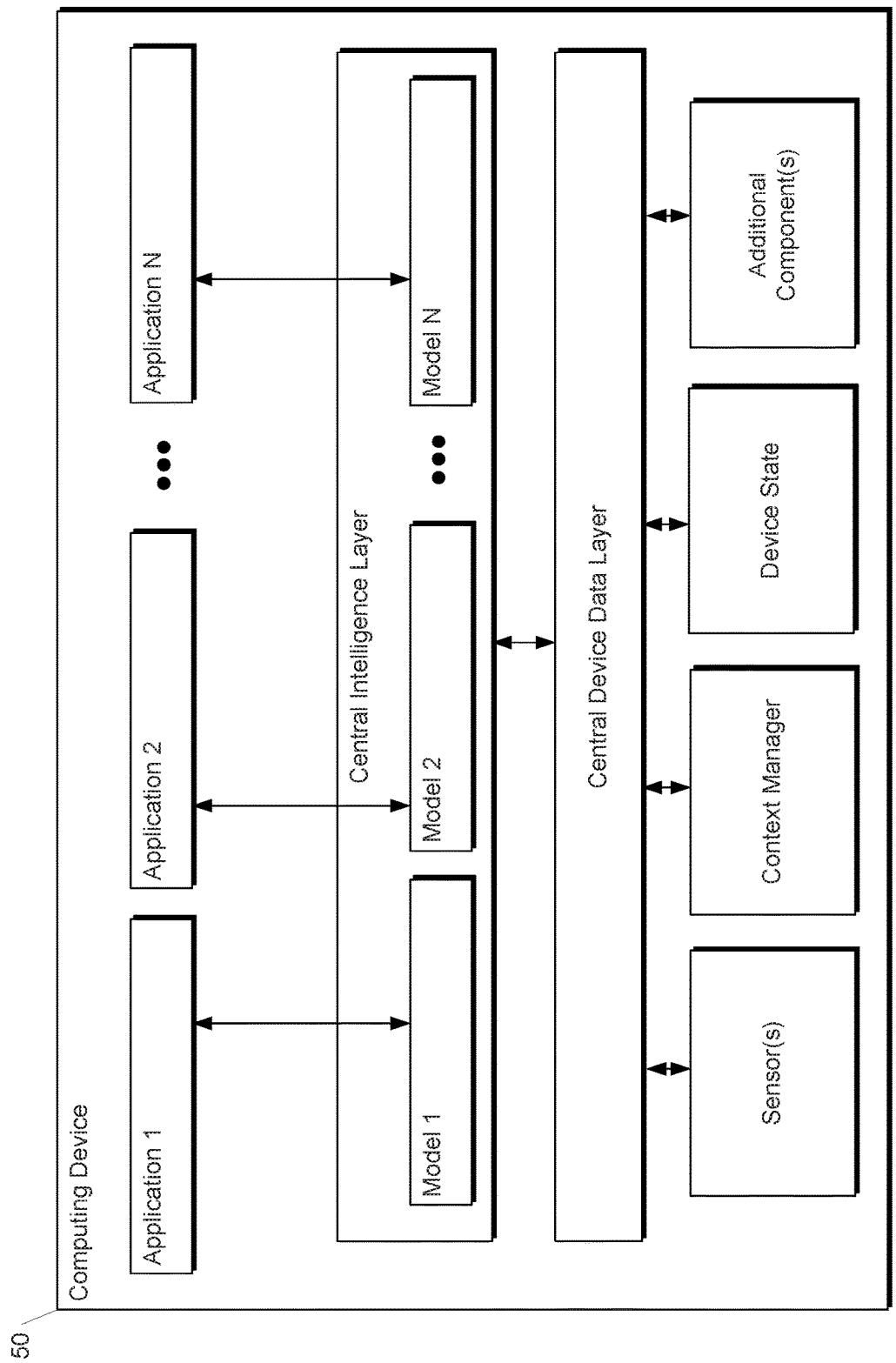
FIG. 1C depicts a block diagram of an example computing device according to example embodiments of the present disclosure.

FIG. 1C depicts a block diagram of an example computing device 50 according to example embodiments of the present disclosure. The computing device 50 can be a user computing device or a server computing device.

The computing device 50 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 1C, a respective machine-learned model (e.g., a model) can be provided for each application and managed by the central intelligence layer. In other implementations, two or more applications can share a single machine-learned model. For example, in some implementations, the central intelligence layer can provide a single model (e.g., a single model) for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 1C, the central device data layer can communicate with a number of other components of the computing device, such as, for example, one or more sensors, a context manager, a device state component, and/or additional components. In some implementations, the central device data layer can communicate with each device component using an API (e.g., a private API).

Example Model Arrangements

FIG. 2 depicts a block diagram of an example prediction model 202 according to example embodiments of the present disclosure. In some implementations, the prediction model 202 is trained to receive a set of input data 204 (e.g., user associated data such as user Internet history, direct sensor data, dedicated sensor data, user location history, etc., current device location, environmental data, time of day) and, as a result of receipt of the input data 204, provide output data 206, for example, disease prediction data (e.g., probability that user is currently infected, probabilities that user contracted the disease at particular combinations of time and geographic location, etc.). Additionally, in some implementations, the prediction model 202 can also receive a set of background health data, for example, prevalence map 208, for use in providing a disease prediction.

FIG. 3 depicts a block diagram of an example machine-learned model 202 according to example embodiments of the present disclosure. The machine-learned model 202 is similar to prediction model 202 of FIG. 2 except that machine-learned model 202 of FIG. 3 is one example model that includes a symptoms prediction model 302 and a disease prediction model 306. In some implementations, the machine-learned prediction model 202 can include a symptoms prediction model 302 that predicts symptoms based on the user-associated data and a disease prediction model 306 that predicts one or more diseases based on symptoms 304. Thus, the models might connect from user data 204 to symptoms 304 and from symptoms 304 to illnesses (e.g., disease prediction 206). Thus, in some implementations, a user device may determine disease/illness symptoms based on the collected data and/or signals.

Example Methods

Figure 4:
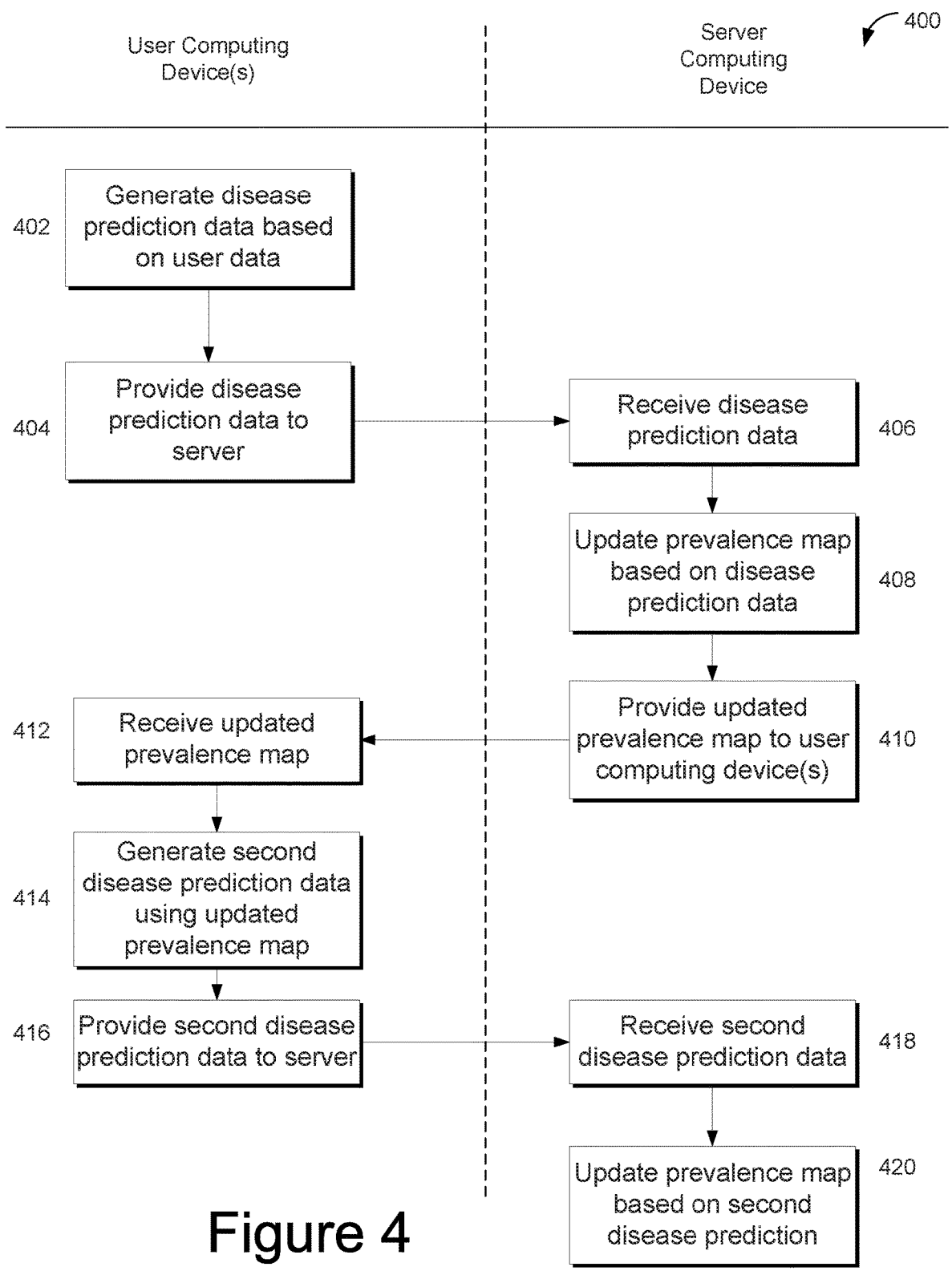
FIG. 4 depicts a flowchart diagram of an example method for federated health modeling and intervention according to example embodiments of the present disclosure.

FIG. 4 depicts a flowchart diagram of example method 400 for federated health modeling and intervention according to example embodiments of the present disclosure. Although FIG. 4 depicts steps performed in a particular order for purposes of illustration and discussion, the methods of the present disclosure are not limited to the particularly illustrated order or arrangement. The various steps of the method 400 can be omitted, rearranged, combined, and/or adapted in various ways without deviating from the scope of the present disclosure. Method 400 can be implemented by one or more computing devices, such as one or more of the computing devices depicted in FIGS. 1A-1C.

At 402, method 400 can include generating, by a user computing device, disease prediction data based at least in part on user-associated data. In particular, a machine-learned prediction model can be implemented locally on a user computer device (e.g., smartphone, tablet, etc.) to predict a probability that the user currently has a disease (e.g., indicates a risk of disease infection, etc.) based on locally stored data that is associated with the user. As examples, this user-associated data can include user Internet history (e.g., submitted queries or other search history), direct sensor data (e.g., microphone data, camera data (e.g., infrared, ultraviolet, and/or visible light video data), accelerometer data, RADAR data, etc.), dedicated sensor data (e.g., heart rate, blood pressure, electrocardiogram, thermal properties, etc.), a user location history, and/or other forms of user data. In some implementations, the user computing device may also provide as input to the machine-learned model or otherwise leverage background health information, such as prevalence maps, for use in predicting whether a user has contracted a disease.

The machine-learned prediction model can be configured to predict a probability that the user may be infected with a disease based at least in part on the user-associated data associated with the user and/or other input data. As one example, the disease prediction can provide a probability that the user currently indicates a risk of disease infection. In another example, the disease prediction can provide, for each of a plurality of combinations of time and geographic location, a respective probability of the user having contracted the disease at such combination of time and geographic location.

At 404, method 400 can include providing, by the user computing device, the disease prediction data to a server computing device, and at 406, method 400 can include receiving, by the server computing device, the disease prediction data. For instance, the user computing device can transmit disease prediction data to a server computing system in a privacy-preserving way (e.g., using secure aggregation and/or differential privacy techniques). In some implementations, if the user so chooses, randomized responses can be provided from the user device to the server computing system and securely aggregated into population-level statistics.

At 408, method 400 can include updating, by the server computing device, a prevalence map (e.g., model prevalence of the disease over a plurality of geographic locations) based at least in part on the received disease prediction data. For instance, federated learning and/or privacy-preserving update techniques can be used to maintain and update a prevalence map over time. In particular, the respective outputs of prediction models across a large number of user devices can be securely aggregated and used to update the disease prevalence map. Through the use of on-device inference (e.g., which does not require transmission of user data from the device) and through the use of privacy-preserving upload techniques, the proposed system can generate a prevalence map that provides up-to-date mapping of prevalence of a disease among a population and/or geographic area. This prevalence map can be used for any number of beneficial uses, including, for example, guiding large-scale disease treatment or mitigation efforts.

At 410, method 400 can include providing the updated prevalence map to each user computing device, and at 412, method 400 can include receiving the updated prevalence map at a user computing device.

At 414, method 400 can include generating, by the user computing device, second disease prediction data using the updated prevalence map.

At 416, method 400 can include providing, by the user computing device, the second disease prediction data to the server computing device, and at 418, method 400 can include receiving, by the server computing device, the second disease prediction data. In particular, the server can receive a plurality of local updates from a plurality of user computing devices.

At 420, method 400 can include again updating, by the server computing device, the prevalence map based at least in part on the received second disease prediction data. Any number of iterations of disease prediction generation and prevalence map updates can be performed. That is, method 400 can be performed iteratively to update the prevalence map based on locally generated disease prediction data over time.

Figure 5:
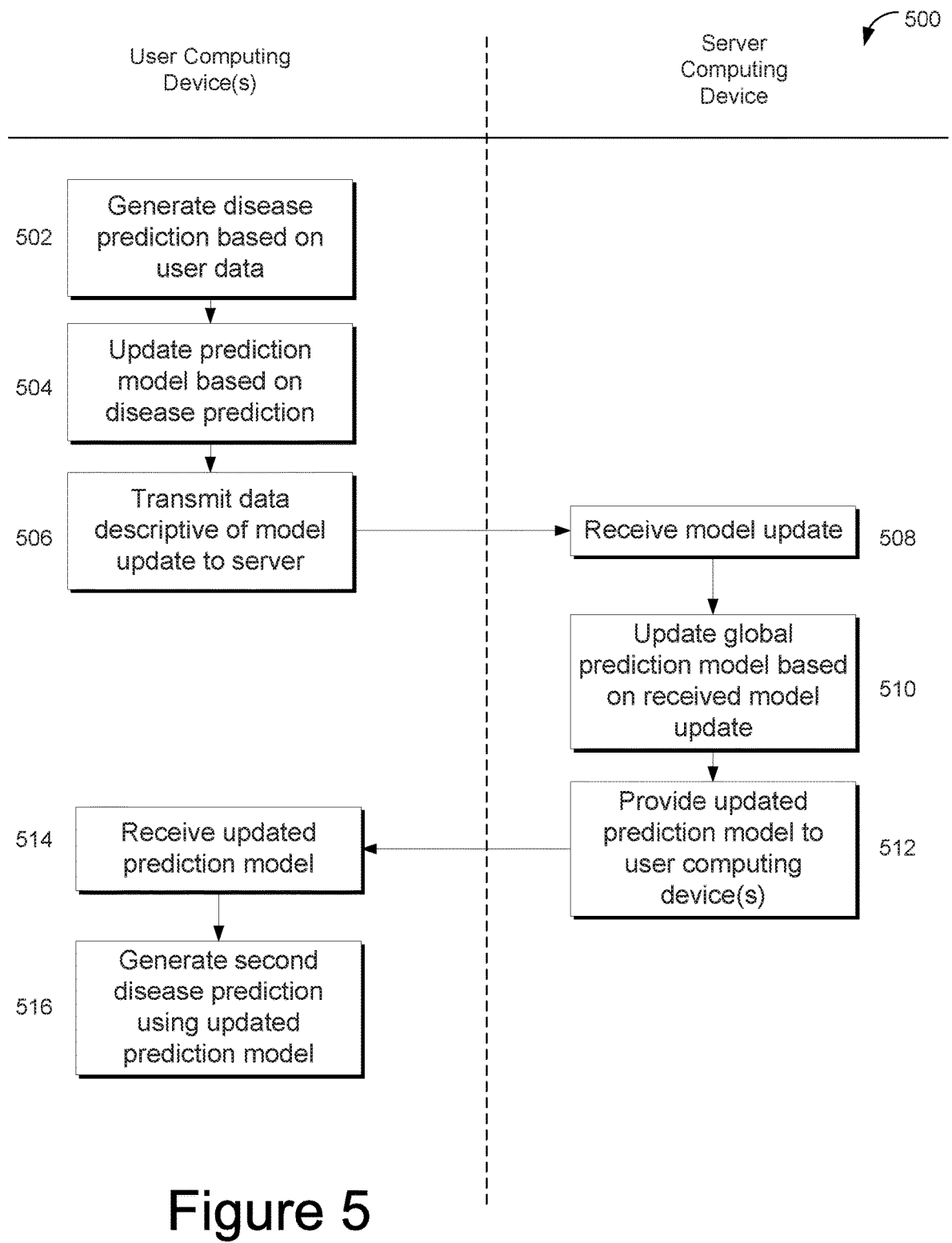
FIG. 5 depicts a flowchart diagram of an example method for federated health modeling and intervention according to example embodiments of the present disclosure.

FIG. 5 depicts a flowchart diagram of example method 500 for federated health modeling and intervention according to example embodiments of the present disclosure. Although FIG. 5 depicts steps performed in a particular order for purposes of illustration and discussion, the methods of the present disclosure are not limited to the particularly illustrated order or arrangement. The various steps of the method 500 can be omitted, rearranged, combined, and/or adapted in various ways without deviating from the scope of the present disclosure. Method 500 can be implemented by one or more computing devices, such as one or more of the computing devices depicted in FIGS. 1A-1C.

At 502, method 500 can include generating, by a user computing device, disease prediction data based at least in part on user-associated data. In particular, a machine-learned prediction model can be implemented locally on a user computer device (e.g., smartphone, tablet, etc.) to predict a probability that the user currently has a disease (e.g., indicates a risk of disease infection, etc.) based on locally stored data that is associated with the user. As examples, this user-associated data can include user Internet history (e.g., submitted queries or other search history), direct sensor data (e.g., microphone data, camera data (e.g., infrared, ultraviolet, and/or visible light video data), accelerometer data, RADAR data, etc.), dedicated sensor data (e.g., heart rate, blood pressure, electrocardiogram, thermal properties, etc.), a user location history, and/or other forms of user data. In some implementations, the user computing device may also provide as input to the machine-learned model or otherwise leverage background health information, such as prevalence maps, for use in predicting whether a user has contracted a disease.

The machine-learned prediction model can be configured to predict a probability that the user may be infected with a disease based at least in part on the user-associated data associated with the user and/or other input data. As one example, the disease prediction can provide a probability that the user is currently infected with the disease. In another example, the disease prediction can provide, for each of a plurality of combinations of time and geographic location, a respective probability of the user having contracted the disease at such combination of time and geographic location.

At 504, method 500 can include updating, by the user computing device, the local prediction model based at least in part on the disease prediction data. For example, updating the model can include modifying data included in the model.

At 506, method 500 can include providing, by the user computing device, data descriptive of the local prediction model update to a server computing device, and at 508, method 500 can include receiving, by the server computing device, the data descriptive of the local prediction model update. For instance, the user computing device can transmit disease prediction data to a server computing system in a privacy-preserving way (e.g., using secure aggregation and/or differential privacy techniques). The user computing device can provide the data indicative of the local prediction model updates to the server computing system to be used in updating a global machine-learned model to infer disease state.

At 510, method 500 can include updating, by the server computing device, a global prediction model based at least in part on the received data descriptive of the local prediction model update. For instance, the global prediction can be updated, for example, according to a federated learning scheme and using the local model updates obtained from a plurality of user computing devices. For example, respective local updates to the machine-learned prediction model across the large number of user devices can be securely aggregated according to a federated learning scheme to improve the accuracy of the global prediction model over time.

At 512, method 500 can include providing the updated prediction model to each user computing device, and at 514, method 500 can include receiving the updated prediction model at a user computing device.

At 516, method 500 can include generating, by the user computing device, second disease prediction data using the updated prediction model based at least in part on user-associated data.

Any number of iterations of local disease predictions, local prediction model updates, and global prediction model updates can be performed. That is, method 500 can be performed iteratively to update the global prediction model based on locally generated prediction model update data over time.

Figure 6:
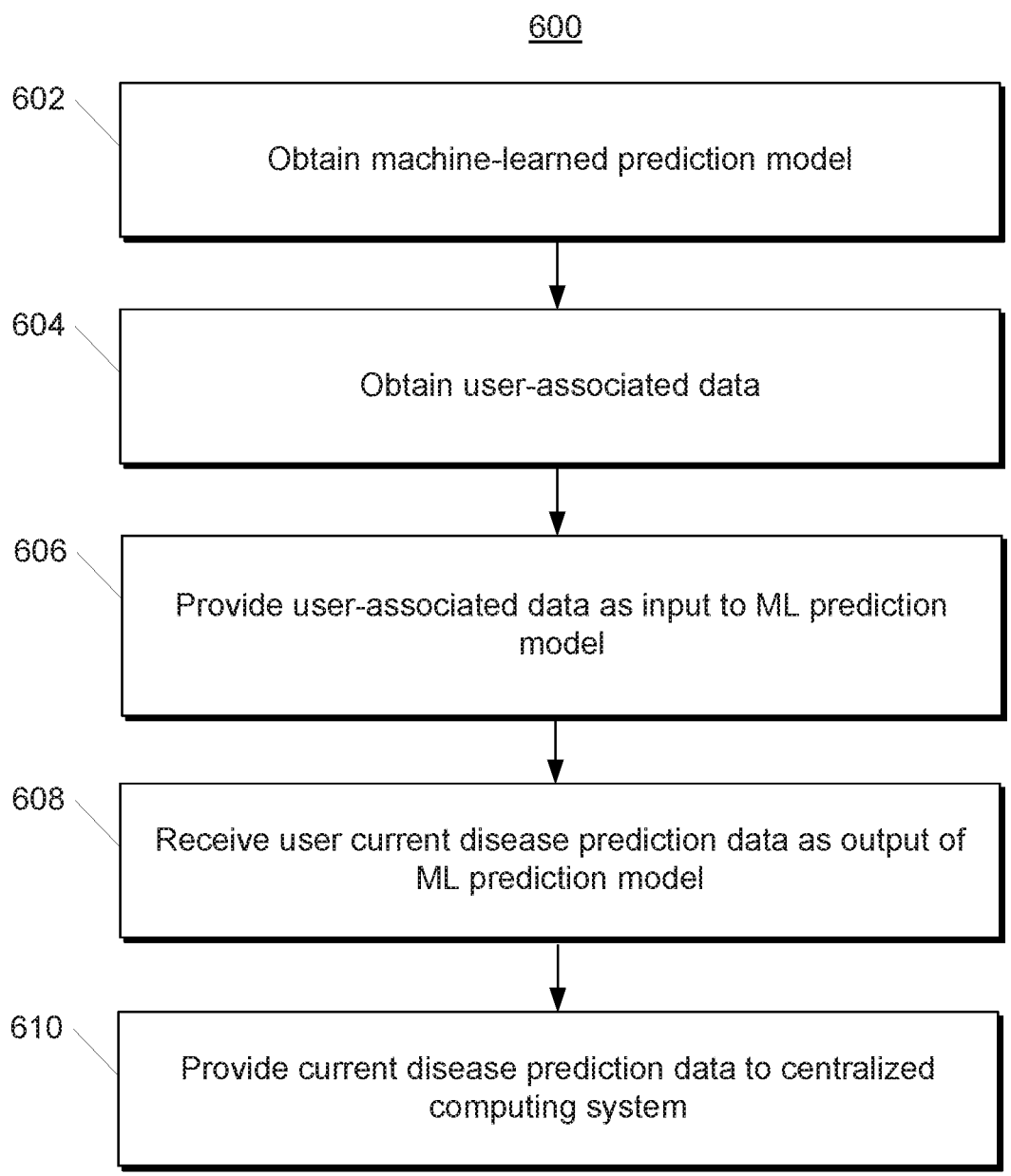
FIG. 6 depicts a flowchart diagram of an example method for disease prediction according to example embodiments of the present disclosure.

FIG. 6 depicts a flowchart diagram of example method 600 for disease prediction according to example embodiments of the present disclosure. Although FIG. 6 depicts steps performed in a particular order for purposes of illustration and discussion, the methods of the present disclosure are not limited to the particularly illustrated order or arrangement. The various steps of the method 600 can be omitted, rearranged, combined, and/or adapted in various ways without deviating from the scope of the present disclosure. Method 600 can be implemented by one or more computing devices, such as one or more of the computing devices depicted in FIGS. 1A-1C.

At 602, a computing system (e.g., user computing device) can obtain a machine-learned prediction model, for example, from a centralized computing system. In particular, a machine-learned prediction model can be implemented locally on a user computer device (e.g., smartphone, tablet, etc.) to predict a probability that the user currently has a disease (e.g., indicates a risk and/or likelihood of disease infection, etc.) based at least in part on locally stored data that is associated with the user.

At 604, the computing system can receive, collect, or otherwise obtain user-associated data. As examples, this user-associated data can include user Internet history (e.g., submitted queries or other search history), direct sensor data (e.g., microphone data, camera data (e.g., infrared, ultraviolet, and/or visible light video data), accelerometer data, RADAR data, etc.), dedicated sensor data (e.g., heart rate, blood pressure, electrocardiogram, thermal properties, etc.), a user location history, and/or other forms of user data. In some implementations, the user computing device may also provide as input to the machine-learned model or otherwise leverage background health information, such as prevalence maps, for use in predicting whether a user has contracted a disease.

At 606, the computing system can input at least the user-associated data into the machine-learned prediction model. In some implementations, the computing system may also provide as input to the machine-learned model or otherwise leverage background health information, such as prevalence maps, for use in predicting whether a user has contracted a disease.

At 608, the computing system can receive user disease prediction data as output of the machine-learned prediction model. The machine-learned prediction model can be configured to predict a probability that the user may be infected with a disease (e.g., indicates a risk and/or likelihood of disease infection) based at least in part on the user-associated data associated with the user and/or other input data. As one example, the disease prediction can provide a probability that the user is currently infected with the disease. In another example, the disease prediction can provide, for each of a plurality of combinations of time and geographic location, a respective probability of the user having contracted the disease at such combination of time and geographic location.

In some implementations, the machine-learned prediction model can include one or both of a symptoms prediction model that predicts symptoms based on the user-associated data and/or a disease prediction model that predicts one or more diseases based on symptoms. Thus, the model(s) might connect from user data to symptoms and/or from symptoms to illnesses. Thus, in some implementations, a user device may determine disease/illness symptoms based on the collected data and/or signals. For example, microphone data may be used in identifying a cough, slurring of speech, lethargy, and/or the like. Camera data may be used in identifying jaundice, swelling, marks, vision difficulty, and/or the like. Accelerometer data may be used in identifying stress, shivering, shaking, lethargy, and/or the like. Alternatively, the prediction model may be a single model configured to predict disease directly from the user data. In any of these configurations, end-to-end training can be used to train on training data that labels user data with disease information.

At 610, the computing system can provide (e.g., based on user consent settings, etc.) the user disease prediction data to a centralized computing system, for example, to provide for use in updating prevalence maps, global prediction models, and/or the like. For example, federated learning and/or privacy-preserving update techniques can be used to maintain and update the prediction model(s) and/or prevalence map(s) over time. For example, the respective outputs of prediction models across a large number of user devices can be securely aggregated and used to update the disease prevalence map. As another example, respective local updates to the machine-learned prediction model across the large number of user devices can be aggregated according to a federated learning scheme to improve the accuracy of the prediction model over time. The updated prediction models and/or prevalence maps can then be sent back to the user devices for more accurate on device disease prediction. Thus, improved user-specific prediction and population-level mapping can be achieved over time while preserving user privacy.

Figure 7:
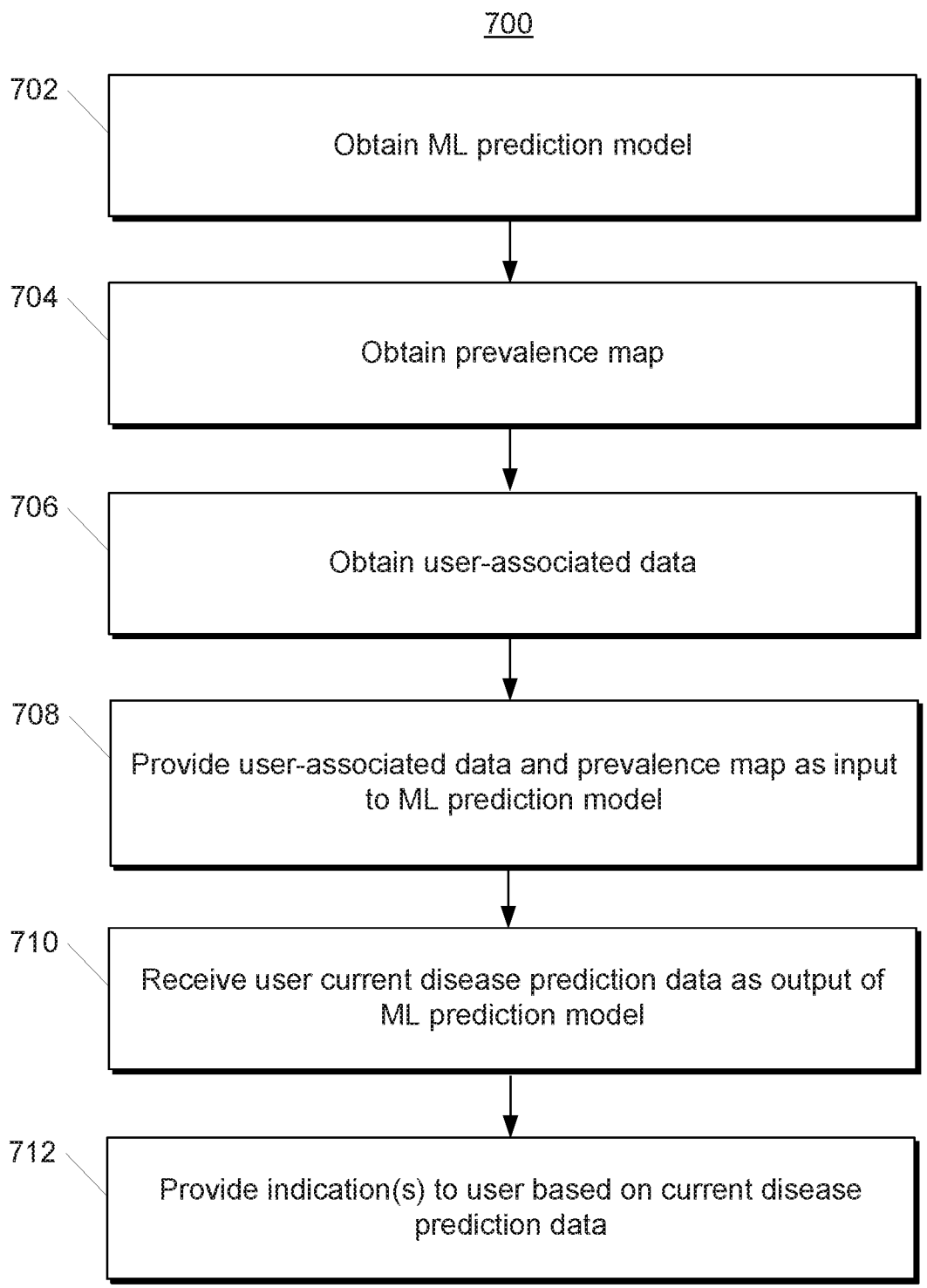
FIG. 7 depicts a flowchart diagram of an example method for disease prediction according to example embodiments of the present disclosure.

FIG. 7 depicts a flowchart diagram of example method 700 for disease prediction according to example embodiments of the present disclosure. Although FIG. 7 depicts steps performed in a particular order for purposes of illustration and discussion, the methods of the present disclosure are not limited to the particularly illustrated order or arrangement. The various steps of the method 700 can be omitted, rearranged, combined, and/or adapted in various ways without deviating from the scope of the present disclosure. Method 700 can be implemented by one or more computing devices, such as one or more of the computing devices depicted in FIGS. 1A-1C.

At 702, a computing system (e.g., user computing device) can obtain a machine-learned prediction model, for example, from a centralized computing system. In particular, a machine-learned prediction model can be implemented locally on a user computer device (e.g., smartphone, tablet, etc.) to predict a probability that the user currently has a disease (e.g., indicates a risk and/or likelihood of disease infection, etc.) based at least in part on locally stored data that is associated with the user.

At 704, the computing system can obtain prevalence map data (e.g., model prevalence of the disease over a plurality of geographic locations), for example, from a centralized computing system.

At 706, the computing system can receive, collect, or otherwise obtain user-associated data. As examples, this user-associated data can include user Internet history (e.g., submitted queries or other search history), direct sensor data (e.g., microphone data, camera data (e.g., infrared, ultraviolet, and/or visible light video data), accelerometer data, RADAR data, etc.), dedicated sensor data (e.g., heart rate, blood pressure, electrocardiogram, thermal properties, etc.), a user location history, and/or other forms of user data. In some implementations, the user computing device may also provide as input to the machine-learned model or otherwise leverage background health information, such as prevalence maps, for use in predicting whether a user has contracted a disease.

At 708, the computing system can input at least the user-associated data and prevalence map data into the machine-learned prediction model.

At 710, the computing system can receive user disease prediction data as output of the machine-learned prediction model. The machine-learned prediction model can be configured to predict a probability that the user may be infected with a disease (e.g., indicates a risk of disease infection) based at least in part on the user-associated data associated with the user, prevalence map data, and/or other input data. As one example, the disease prediction can provide a probability that the user is currently infected with the disease. In another example, the disease prediction can provide, for each of a plurality of combinations of time and geographic location, a respective probability of the user having contracted the disease at such combination of time and geographic location.

At 712, the computing system can provide one or more indications to the user based on the user disease prediction data. In some implementations, on-device disease prediction may allow for providing one or more indications to a user based on a prediction of contracting an illness. For example, the computing system (e.g., user computing device) can inform the user of the likelihood of infection and suggest remedial actions, such as visiting medical professionals, reducing risk behaviors, and/or the like.

Figure 8:
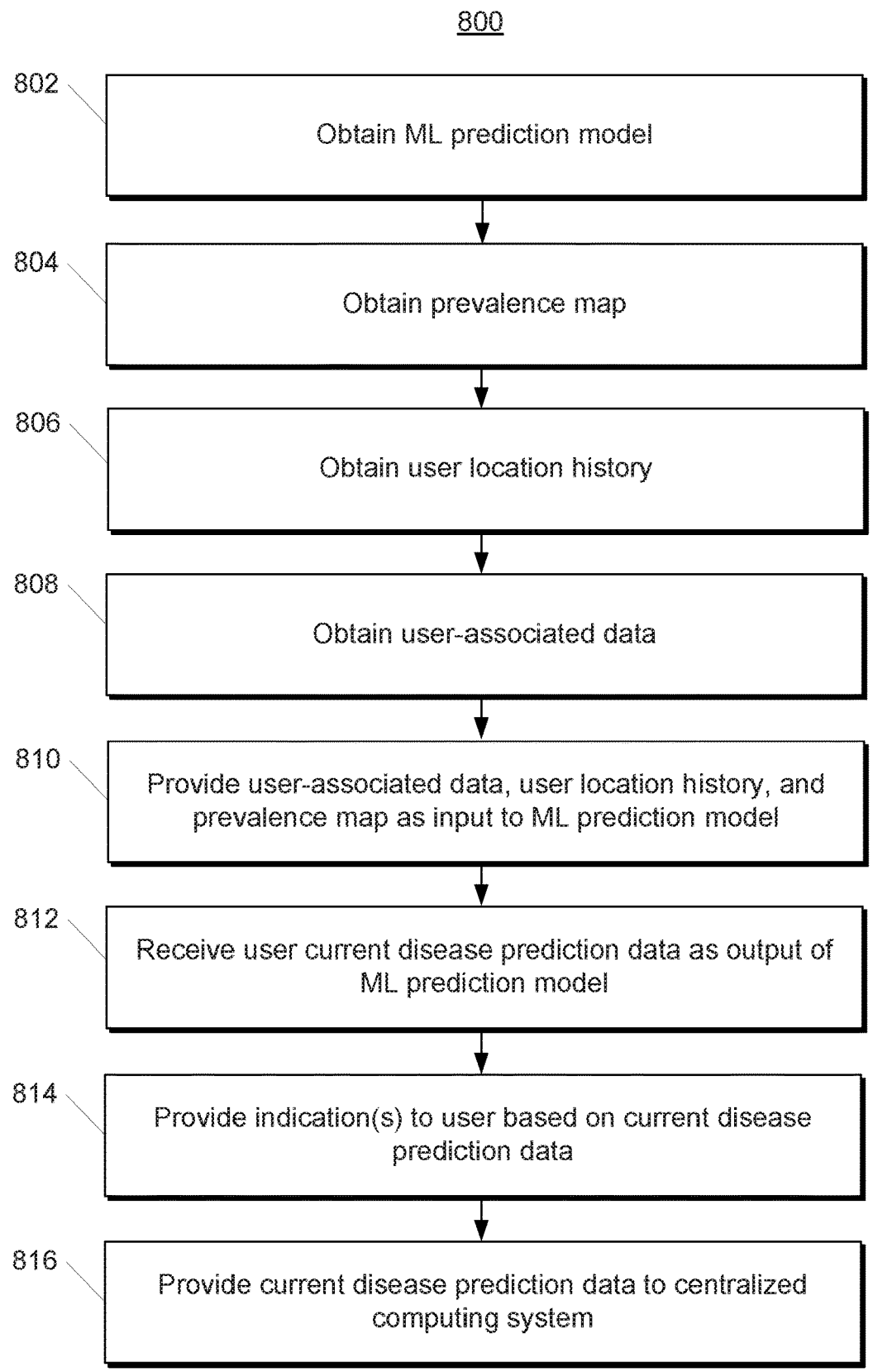
FIG. 8 depicts a flowchart diagram of an example method for disease prediction according to example embodiments of the present disclosure.

FIG. 8 depicts a flowchart diagram of example method 800 for disease prediction according to example embodiments of the present disclosure. Although FIG. 8 depicts steps performed in a particular order for purposes of illustration and discussion, the methods of the present disclosure are not limited to the particularly illustrated order or arrangement. The various steps of the method 800 can be omitted, rearranged, combined, and/or adapted in various ways without deviating from the scope of the present disclosure. Method 800 can be implemented by one or more computing devices, such as one or more of the computing devices depicted in FIGS. 1A-1C.

At 802, a computing system (e.g., user computing device) can obtain a machine-learned prediction model, for example, from a centralized computing system. In particular, a machine-learned prediction model can be implemented locally on a user computer device (e.g., smartphone, tablet, etc.) to predict a probability that the user currently has a disease (e.g., indicates a risk and/or likelihood of disease infection, etc.) based at least in part on locally stored data that is associated with the user.

At 804, the computing system can obtain prevalence map data (e.g., model prevalence of the disease over a plurality of geographic locations), for example, from a centralized computing system.

At 806, the computing system can obtain user location history data.

At 808, the computing system can receive, collect, or otherwise obtain user-associated data. For example, the user device can obtain pertinent on-device user-associated data and signals (e.g., device location, user query history, general sensor data, dedicated sensor data descriptive of user physical attributes, environmental data, time of day, etc.) obtained from one or more sensors, generated, and/or stored on the user device.

At 810, the computing system can input at least the user-associated data, user location history data, and prevalence map data into the machine-learned prediction model.

At 812, the computing system can receive user disease prediction data as output of the machine-learned prediction model. The machine-learned prediction model can be configured to predict a probability that the user may be infected with a disease (e.g., indicates a risk of disease infection) based at least in part on the user-associated data associated with the user, user location history, prevalence map data, and/or other input data. As one example, the disease prediction can provide a probability that the user is currently infected with the disease. In another example, the disease prediction can provide, for each of a plurality of combinations of time and geographic location, a respective probability of the user having contracted the disease at such combination of time and geographic location.

At 814, the computing system can provide one or more indications to the user based on the user disease prediction data. In some implementations, on-device disease prediction may allow for providing one or more indications to a user based on a prediction of contracting an illness. For example, the computing system (e.g., user computing device) can inform the user of the likelihood of infection and suggest remedial actions, such as visiting medical professionals, reducing risk behaviors, and/or the like.

At 816, the computing system can provide (e.g., based on user consent settings, etc.) the user disease prediction data to a centralized computing system, for example, to provide for use in updating prevalence maps, global prediction models, and/or the like.

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method to perform privacy-preserving on-device federated health modeling, the method comprising:

obtaining, by a user computing device associated with a user, a machine-learned prediction model configured to predict a probability that the user is infected with a disease based at least in part on user-associated data associated with the user;

receiving, by the user computing device, the user-associated data associated with the user, wherein the user-associated data is collected by the user computing device and stored locally at the user computing device;

providing, by the user computing device, the user-associated data as input to the machine-learned prediction model, the machine-learned prediction model being implemented on the user computing device;

generating, by the user computing device, a current disease prediction for the user as an output of the machine-learned prediction model implemented on the user computing device;

performing by the user computing device, a differential privacy technique on the current disease prediction, wherein performing the differential privacy technique comprises:
    drawing, by the user computing device, noise from a probability distribution; and
    adding, by the user computing device, the noise to the current disease prediction to generate noisy signal data based on the current disease prediction; and
    transmitting, by the user computing device, a response based on the noisy signal data to a central computing system for use in centrally updating, by the central computing system, a prevalence map that models prevalence of the disease over a plurality of geographic locations, wherein the response transmitted by the user computing device to the central computing system excludes the user-associated data such that the user-associated data does not leave the user computing device.

2. The computer-implemented method of claim 1, further comprising, prior to transmitting the response based on the noisy signal data to the central computing system for use in updating the prevalence map:
    obtaining, by the user computing device, the prevalence map from the central computing system;
    obtaining, by the user computing device, a location history associated with the user; and
    providing, by the user computing device, the prevalence map and the location history as input to the machine-learned prediction model alongside the user-associated data, the current disease prediction output by the machine-learned prediction model being based at least in part on each of the user-associated data, the location history associated with the user, and the prevalence map.

3. The computer-implemented method of claim 1, further comprising:
    obtaining, by the user computing device, the prevalence map from the central computing system, wherein the prevalence map models prevalence of the disease over the plurality of geographic locations and also over time; and
    generating, by the user computing device, for each of a plurality of combinations of time and geographic location, a respective probability of the user having contracted the disease at such combination of time and geographic location based at least in part on the prevalence map.

4. The computer-implemented method of claim 1, wherein transmitting, by the user computing device, the response based on the noisy signal data to the central computing system for use in updating the prevalence map comprises performing, by the user computing device, a secure aggregation technique or a differential privacy technique to provide the data indicative of the current disease prediction for the user to the central computing system.

5. The computer-implemented method of claim 4, wherein performing, by the user computing device, the secure aggregation technique or the differential privacy technique to provide the data indicative of the current disease prediction for the user to the central computing system comprises:
    providing, by the user computing device with a first probability, the data indicative of the current disease prediction for the user to the central computing system; and
    providing, by the user computing device with a second probability, a falsified disease prediction for the user to the central computing system.

6. The computer-implemented method of claim 1, wherein the user-associated data comprises one or more of:
    a device location of the user computing device;
    a search engine query history associated with the user;
    sensor data that is descriptive of a physical attribute of the user;
    environmental conditions associated with a current location of the user; and
    a time of day.

7. The computer-implemented method of claim 6, wherein the sensor data comprises one or more of:
    audio data descriptive of a vocalization of the user;
    image data that depicts the user;
    accelerometer data descriptive of motion of the user;
    heart rate data;
    blood pressure data; and
    electrocardiogram data.

8. The computer-implemented method of claim 1, wherein the machine-learned prediction model comprises one or both of:
    a symptoms prediction model that predicts symptoms based on user-associated data; and
    a disease prediction model that predicts one or more diseases based on symptoms.

9. The computer-implemented method of claim 1, wherein the machine-learned prediction model has been trained using ground truth public health data.

10. The computer-implemented method of claim 1, further comprising:
    re-training, by the user computing device, the machine-learned prediction model based at least in part on a loss function that evaluates a difference between the current disease prediction for the user and a label,
    transmitting, by the user computing device, a model update descriptive of one or more changes to the machine-learned prediction model made during the re-training to the central computing system for use in determining an aggregate update to the machine-learned prediction model; and
    receiving, by the user computing device or another computing device, an updated version of the machine-learned prediction model from the central computing system, the updated version of the machine-learned prediction model based at least in part on the aggregate update.

11. The computer-implemented method of claim 1, further comprising:
    providing, by the user computing device, one or more notifications to the user based at least in part on the current disease prediction.

12. The computer-implemented method of claim 1, further comprising:
    maintaining, by the central computing system, a record of changes to the prevalence map over time; and
    training, by the central computing system, an additional machine-learned model based on the record of changes to the prevalence map to configure the additional machine-learned model to predict one or more future changes to one or more future prevalence maps.

13. The computer-implemented method of claim 1, wherein the noisy signal data is configured to preserve population-level trends.

14. The computer-implemented method of claim 1, wherein the prevalence map satisfies a differential privacy guarantee with respect to the current disease prediction.

15. The computer-implemented method of claim 1, wherein the probability distribution comprises a Laplacian distribution, and wherein adding the noise to the current disease prediction comprises bounding a probability of a different output of the machine-learned prediction model without the user-associated data.

16. A computing device configured to perform privacy-preserving on-device federated health modeling, comprising:
one or more processors; and
one or more non-transitory computer-readable media that store instructions that, when executed by the one or more processors, cause the computing device to perform operations, the operations comprising:
obtaining a machine-learned prediction model configured to predict a probability that a user is infected with a disease based at least in part on user-associated data associated with the user,
receiving a prevalence map and one or more types of user-associated data, wherein the prevalence map models prevalence of the disease over a plurality of geographic locations, and wherein the user-associated data is collected by the computing device and stored locally at the computing device;
providing the one or more types of user-associated data and the prevalence map as input to the machine-learned prediction model;
generating a current disease prediction for the user as an output of the machine-learned prediction model;
providing one or more indications to the user based the current disease prediction;
performing a differential privacy technique on the current disease prediction, wherein performing the differential privacy technique comprises:
drawing noise from a probability distribution; and
adding the noise to the current disease prediction to generate noisy signal data based on the current disease prediction; and
transmitting a response based on the noisy signal data to a central computing system for use in centrally updating the prevalence map, wherein the response transmitted by the computing device to the central computing system excludes the user-associated data such that the user-associated data does not leave the computing device.

17. The computing device of claim 16, wherein the current disease prediction provided as an output of the machine-learned prediction model comprises a probability of being infected; and a probability of having contracted an infection for each of one or more time and geographic buckets considered by the machine-learned prediction model.

18. The computing device of claim 17, wherein the operations further comprise:
providing data indicative of the probability of having contracted an infection for each of one or more time and geographic buckets considered by the machine-learned prediction model for use in updating the prevalence map.

19. The computing device of claim 18, wherein the central computing system aggregates the data indicative of the probability of having contracted the infection for each of one or more time and geographic buckets in a secure manner to update the prevalence map.

20. The computing device of claim 18, wherein providing data indicative of the probability of having contracted an infection for each of one or more time and geographic buckets considered by the machine-learned prediction model for use in updating the prevalence map includes providing randomized probabilities for one or more of the time and geographic buckets.

21. A computer-implemented method to perform privacy-preserving on-device federated health modeling, the method comprising:
obtaining, by a user computing device associated with a user, a machine-learned prediction model configured to predict a probability that the user is infected with a disease based at least in part on user-associated data associated with the user;
receiving, by the user computing device, a prevalence map and the user-associated data associated with the user, wherein the prevalence map models prevalence of the disease over a plurality of geographic locations, and wherein the user-associated data is collected by the user computing device and stored locally at the user computing device;
providing, by the user computing device, the user-associated data and the prevalence map as input to the machine-learned prediction model, the machine-learned prediction model being implemented on the user computing device;
generating, by the user computing device, a current disease prediction for the user as an output of the machine-learned prediction model;
providing, by the user computing device, one or more notifications to the user based at least in part on the current disease prediction;
performing, by the user computing device, a differential privacy technique on the current disease prediction, wherein performing the differential privacy technique comprises;
drawing, by the user computing device, noise from a probability distribution; and
adding the noise to the current disease prediction to generate noisy signal data based on the current disease prediction; and
transmitting, by the user computing device, a response based on the noisy signal data to a central computing system for use in updating the prevalence map, wherein the response transmitted by the user computing device to the central computing system excludes the user-associated data such that the user-associated data does not leave the user computing device.

22. The computer-implemented method of claim 21, wherein the user-associated data comprises one or more of:
a device location of the user computing device;
a search engine query history associated with the user;
sensor data that is descriptive of a physical attribute of the user;
environmental conditions associated with a current location of the user; and
a time of day.

23. The computer-implemented method of claim 22, wherein the sensor data comprises one or more of:
audio data descriptive of a vocalization of the user;
image data that depicts the user;
accelerometer data descriptive of motion of the user;
heart rate data;
blood pressure data; and
electrocardiogram data.

24. The computer-implemented method of claim 21, wherein the machine-learned prediction model comprises one or both of:
 a symptoms prediction model that predicts symptoms based on user-associated data; and
 a disease prediction model that predicts one or more diseases based on symptoms.

\* \* \* \* \*